US011158427B2

(12) United States Patent
Ma et al.

(10) Patent No.: US 11,158,427 B2
(45) Date of Patent: Oct. 26, 2021

(54) MACHINE LEARNING FOR MEDICAL SCREENING RECOMMENDATIONS BASED ON PATIENT ACTIVITY INFORMATION IN SOCIAL MEDIA

(71) Applicant: International Business Machines Corporation, Armonk, NY (US)

(72) Inventors: Ryan Ma, Somerville, MA (US); Raghavendra Mujumdar, Boston, MA (US); William G. O'Keeffe, Tewksbury, MA (US); Ravi Tejwani, Cambridge, MA (US)

(73) Assignee: International Business Machines Corporation, Armonk, NY (US)

( * ) Notice: Subject to any disclaimer, the term of this patent is extended or adjusted under 35 U.S.C. 154(b) by 344 days.

(21) Appl. No.: 15/656,406

(22) Filed: Jul. 21, 2017

(65) Prior Publication Data

US 2019/0026438 A1    Jan. 24, 2019

(51) Int. Cl.
   *G16H 50/30*    (2018.01)
   *G16H 50/20*    (2018.01)
   (Continued)

(52) U.S. Cl.
   CPC ............ *G16H 50/30* (2018.01); *G16H 10/60* (2018.01); *G16H 40/67* (2018.01); *G16H 50/20* (2018.01); *G16H 50/50* (2018.01); *G06Q 50/01* (2013.01)

(58) Field of Classification Search
   CPC .... G06F 19/3418; G16H 50/20; G16H 10/60; G16H 10/00; G16H 50/30; G06Q 50/01
   (Continued)

(56) References Cited

U.S. PATENT DOCUMENTS 7,899,764 B2 *  3/2011  Martin ................... G16H 30/20
                                                        706/12
8,706,530 B2    4/2014  Ohnemus et al.
                (Continued)

FOREIGN PATENT DOCUMENTS

KR      20140008878 A  *  1/2014
WO         2014064053 A2    5/2014
WO         2014110120 A1    7/2014

OTHER PUBLICATIONS

Gunther, E., Tim, K., Anis, F. et al. Understanding the Factors that Influence the Adoption and Meaningful Use of Social Media by Physicians to Share Medical Information. Journal of Medical Internet Research, 14(5), e117. Sep. 2012, 10 pages.
(Continued)

*Primary Examiner* — Mark Holcomb
(74) *Attorney, Agent, or Firm* — Ryan Lewis; Edell, Shapiro & Finnan, LLC

(57) ABSTRACT

According to an embodiment of the present invention, a system analyzes a collection of medical documents to identify within document content risk factors of medical conditions associated with corresponding activities. A processor in the system maps the identified risk factors of the activities to one or more medical tests for the associated medical conditions, and analyzes a medical record and social media communications of a patient to determine participation of the patient in one or more of the corresponding activities. The processor determines the one or more medical tests to conduct from the mapping based on the risk factors associated with the determined activities of the patient. Embodiments of the present invention further include a method and computer program product for analyzing patient activity to conduct appropriate medical tests in substantially the same manner described above.

17 Claims, 6 Drawing Sheets

(51) Int. Cl.
*G16H 10/60* (2018.01)
*G16H 40/67* (2018.01)
*G16H 50/50* (2018.01)
*G06Q 50/00* (2012.01)

(58) Field of Classification Search
USPC .......................................................... 705/2–4
See application file for complete search history.

(56) References Cited

U.S. PATENT DOCUMENTS

| | | | | |
|---|---|---|---|---|
| 9,910,962 | B1* | 3/2018 | Fakhrai-Rad | G16H 50/20 |
| 2009/0018863 | A1* | 1/2009 | Yoon | G06Q 40/08 705/2 |
| 2010/0094648 | A1* | 4/2010 | Seward | G16H 50/20 705/2 |
| 2011/0161110 | A1* | 6/2011 | Mault | G16H 40/67 705/3 |
| 2013/0086163 | A1 | 4/2013 | Neff | |
| 2014/0058754 | A1 | 2/2014 | Wild | |
| 2014/0372133 | A1* | 12/2014 | Austrum | G16H 20/60 705/2 |
| 2015/0018630 | A1 | 1/2015 | Fotuhi | |
| 2015/0120633 | A1 | 4/2015 | Norlander et al. | |
| 2015/0363568 | A1* | 12/2015 | Milo | G16H 50/30 705/2 |
| 2016/0055319 | A1* | 2/2016 | Ikegaya | G06Q 40/08 705/3 |
| 2016/0180043 | A1* | 6/2016 | Federoff | G06Q 50/01 705/2 |
| 2016/0287152 | A1 | 10/2016 | Schwartz et al. | |
| 2017/0140114 | A1* | 5/2017 | Are | G06N 20/00 |

OTHER PUBLICATIONS

Chantal, C.G. The Changing Face(book) of Psychiatry: Can We Justify following Patients' Social Media Activity? BJPsych Bulletin, 39(6), 283-284, Dec. 2015.

Liu et al., Identifying Adverse Drug Events from Health Social Media: A Case Study on Heart Disease Discussion Forums. Springer Link, Smart Health, vol. 8549 of the series Lecture Notes in Computer Science, pp. 25-36, retrieved from internet May 11, 2016, https://books.google.com/books?id=rF8IBAAAQBAJ&lpg=PA25 &dq=identifying%20medical%20risk%20factors%20from%20social% 20media&pg=PA25#v=onepage&q=identifying%20medical%20risk% 20factors%20from%20social%20media&f=false.

Preventing occupational exposure to lead and noise at indoor firing ranges. NIOSH Alert 2009. Cincinnati, OH: US Department of Health and Human Services, CDC, National Institute for Occupational Safety and Health; Apr. 2009, 32 pages. Available at http://www.cdc.gov/niosh/docs/2009-136/pdfs/2009-136.pdf.

Adult Blood Lead Epidemiology and Surveillance (ABLES). Cincinnati, OH: US Department of Health and Human Services, CDC, National Institute for Occupational Safety and Health; 2013, 4 pages. Available at http://www.cdc.gov/niosh/topics/ables/description.html.

Occupational Safety and Health Administration. Lead standards: general industry (29 CFR 1910.1025) and construction industry (29 CFR 1926.62). Washington, DC: US Department of Labor, Occupational Safety and Health Administration; 1978, 2 pages. Available at https://www.osha.gov/sltc/lead, http://www.cdc.gov/Other/disclaimer.html.

The Shooting Sports. National Shooting Sports Foundation, Inc., Newtown, CT, 2014, 1 page. Available at http://www.nssf.org/shooting/sports, http://www.cdc.gov/Other/disclaimer.html.

Permissible exposure limits—annotated tables. Occupational Safety and Health Administration. Washington, DC: US Department of Labor, Occupational Safety Administration; 2014, 2 pages. Available at https://www.osha.gov/dsg/annotated-pels/index.html, http://www.cdc.gov/Other/disclaimer.html.

Chen I. Overlooked: Thousands of Americans exposed to dangerous levels of lead in their jobs. Scientific American, Aug. 20, 2013, 12 pages. Available at http://www.scientificamerican.com/article/overlooked-thousands-of-american-axposed-to-dangerous-levels-of-lead-in-their-jobs/?page=1, http://www.cdc.gov/Other/disclaimer.html.

Health effects of low-level lead. National Toxicology Program. Research Triangle Park, NC: US Department of Health and Human Services, NIH Publication No. 12-5996, ISSN 2330-1279. 2013, 176 pages.

Billingsley KJ. Letter of Sep. 30, 2013, from K. J. Billingsley, California Department of Public Health, to Juliann Sum, Division of Occupational Safety and Health (Cal/OSHA), California Department of Industrial Relations. Re: Health-based permissible exposure limit for lead. Available at http://www.cdph.ca.gov/programs/olppp/documents/leadstdpelrec.pdf, http://www.cdc.gov/Other/disclaimer.html.

Kosnett MJ, Wedeen, RP, Rothenberg SJ, et al. Recommendations for medical management of adult lead exposure. Environmental Health Perspectives, vol. 115, No. 3, Mar. 2007, pp. 463-471.

Billingsley KJ. Letter of Sep. 30, 2013, from K. J. Billingsley, California Department of Public Health, to Juliann Sum, Division of Occupational Safety and Health (Cal/OSHA), California Department of Industrial Relations. Re: Health-based permissible exposure limit for lead. Available at http://www.cdph.ca.gov/programs/olppp/documents/leadstdpelrec.pdf, http://www.cdc.gov/Other/disclaimer.html, 6 pages.

* cited by examiner

| RISK FACTOR 1 | RISK FACTOR 2 | RISK FACTOR 3 | RISK FACTOR 4 | LAB TEST / PROCEDURE |
|---|---|---|---|---|
| 1 | 1 | 0 | 0 | TEST 1 |
| 0 | 1 | 1 | 0 | TEST 2 |
| 0 | 1 | 0 | 1 | TEST 2 |

FIG.5

MACHINE LEARNING FOR MEDICAL SCREENING RECOMMENDATIONS BASED ON PATIENT ACTIVITY INFORMATION IN SOCIAL MEDIA

BACKGROUND

1. Technical Field

Present invention embodiments relate to machine learning and, more specifically, to recommending medical tests (e.g., medical lab or other tests, medical or other procedures, etc.) based on machine learning inferring the appropriate medical tests from patient activity information in social media.

2. Discussion of the Related Art

Many people are involved in physical activities related to their jobs, hobbies, and/or sporting interests that may make them vulnerable to certain medical conditions. Unfortunately, persons are often unaware of the elevated health risks associated with their activities. When consulting with a physician, therefore, such patients may not consider their personal and/or professional activities relevant to their medical history. As a result, many medical tests that should be part of their regular medical examinations may be omitted, possibly leading to serious medical conditions.

SUMMARY

According to an embodiment of the present invention, a system analyzes a collection of medical documents to identify within document content risk factors of medical conditions associated with corresponding activities. A processor in the system maps the identified risk factors of the activities to one or more medical tests for the associated medical conditions, and analyzes a medical record and social media communications of a patient to determine participation by the patient in one or more of the corresponding activities. The processor determines the one or more medical tests to conduct from the mapping based on the risk factors associated with the determined activities of the patient. Embodiments of the present invention further include a method and computer program product for analyzing patient activity to conduct appropriate medical tests in substantially the same manner described above.

BRIEF DESCRIPTION OF THE DRAWINGS

FIG. 5 is a diagrammatic illustration of an example mapping between risk factors of medical conditions and medical tests produced by a model according to an embodiment of the present invention.

DETAILED DESCRIPTION

Present invention embodiments identify risk factors of medical conditions associated with one or more corresponding activities and, based on patient participation in the activities, dynamically recommends one or more medical tests (e.g., medical lab or other tests, medical or other procedures, etc.). Initially, a server reviews a collection of medical documents to identify one or more risk factors (or activities) associated with one or medical conditions, and correlates the one or more risk factors (or activities) with one or more corresponding medical tests. The server may further review patient activity information in electronic medical records (EMR) and/or social media data to determine whether the patient has an elevated risk of one or more medical conditions based on the patient activity information. When it is determined that the patient has an elevated risk of one or more medical conditions, the server may dynamically recommend one or more medical tests (e.g., medical lab or other tests, medical or other procedures, etc.) associated with the one or more medical conditions.

An embodiment of the present invention may employ a cognitive medical system (e.g., an IBM Watson Health pipeline, IBM Watson Concept Insights, etc.) to perform Natural Language Processing (NLP) techniques to analyze a corpus of medical documents. When a patient visits a physician or other medical service provider, an electronic medical record (EMR) of the patient and patient social media data are mined to identify potential risk factors for medical conditions. The mined information is provided to a machine learning model trained to identify medical tests (e.g., medical lab or other tests, medical or other procedures, etc.) that may need to be performed based on the patient activities identified in the mined information. Recommendations for the medical tests are provided to the physician for medical screening of the patient.

Figure 1:
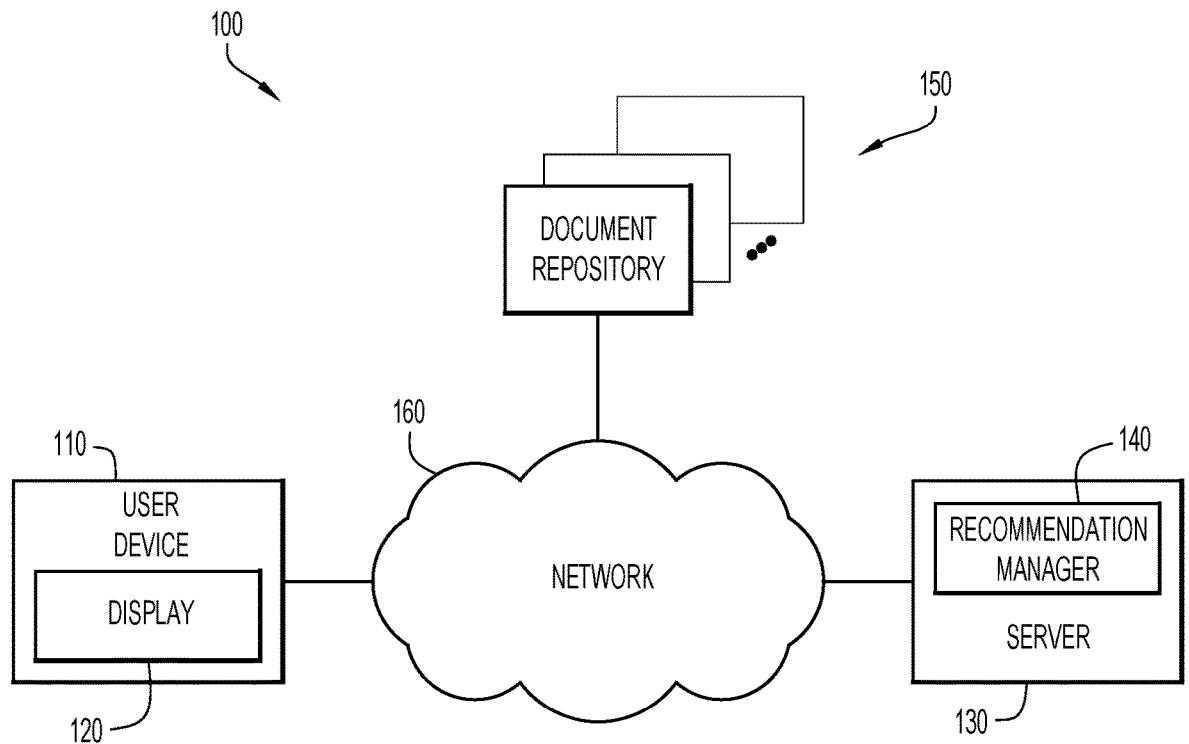
FIG. 1 is a diagrammatic illustration of an example computing environment for use with an embodiment of the present invention.

An example computing environment for use with present invention embodiments is illustrated in FIG. 1. Specifically, environment 100 includes one or more user devices 110, one or more servers 130, and one or more document repositories 150. Servers 130 may comprise a recommendation manager 140 that is responsible for mapping one or more risk factors (or activities) associated with medical conditions identified in a collection of medical or other documents to one or more medical tests. Servers 130 and user devices 110 may be remote from each other and communicate over a network 160. Network 160 may be implemented by any number of any suitable communications media (e.g., wide area network (WAN), local area network (LAN), Internet, Intranet, etc.). Alternatively, servers 130 and user devices 110 may be local to each other, and communicate via any appropriate local communication medium (e.g., local area network (LAN), hardwire, wireless link, Intranet, etc.).

User devices 110 enable users to receive one or more recommendations generated by servers 130 for one or more medical tests (e.g., medical lab or other tests, medical or other procedures, etc.), and to display the one or more recommendations on a display 120. For example, a user device 110 may receive a recommendation from a server 130 for one more or medical tests (e.g., medical lab or other tests, medical or other procedures, etc.) related to elevated blood lead levels. This recommendation may be determined based on patient activity information in social media data indicating that the patient has participated in certain activities involving handling of a firearm.

Initially, a server 130 may receive a request from a user device 110 to generate medical test recommendations based on activity information associated with a patient. After receiving the request from user device 110, server 130 may analyze an electronic medical record (EMR) of the patient and mine patient social media data for patient activity information. Server 130 may determine whether the patient is at risk to develop one or more medical conditions based on previously determined risk factors (or activities) associated with the medical conditions. When server 130 determines that the patient is at risk for developing the one or more medical conditions, server 130 may generate a response to the request that includes one or more recommendations identifying one or more medical tests (e.g., medical lab or other tests, medical or other procedures, etc.) related to the one or more medical conditions. The one or more recommendations are forwarded to user device 110 for display to a user associated with user device 110 (e.g., medical service provider, insurance representative, etc.) on a user interface of display 120.

Figure 2:
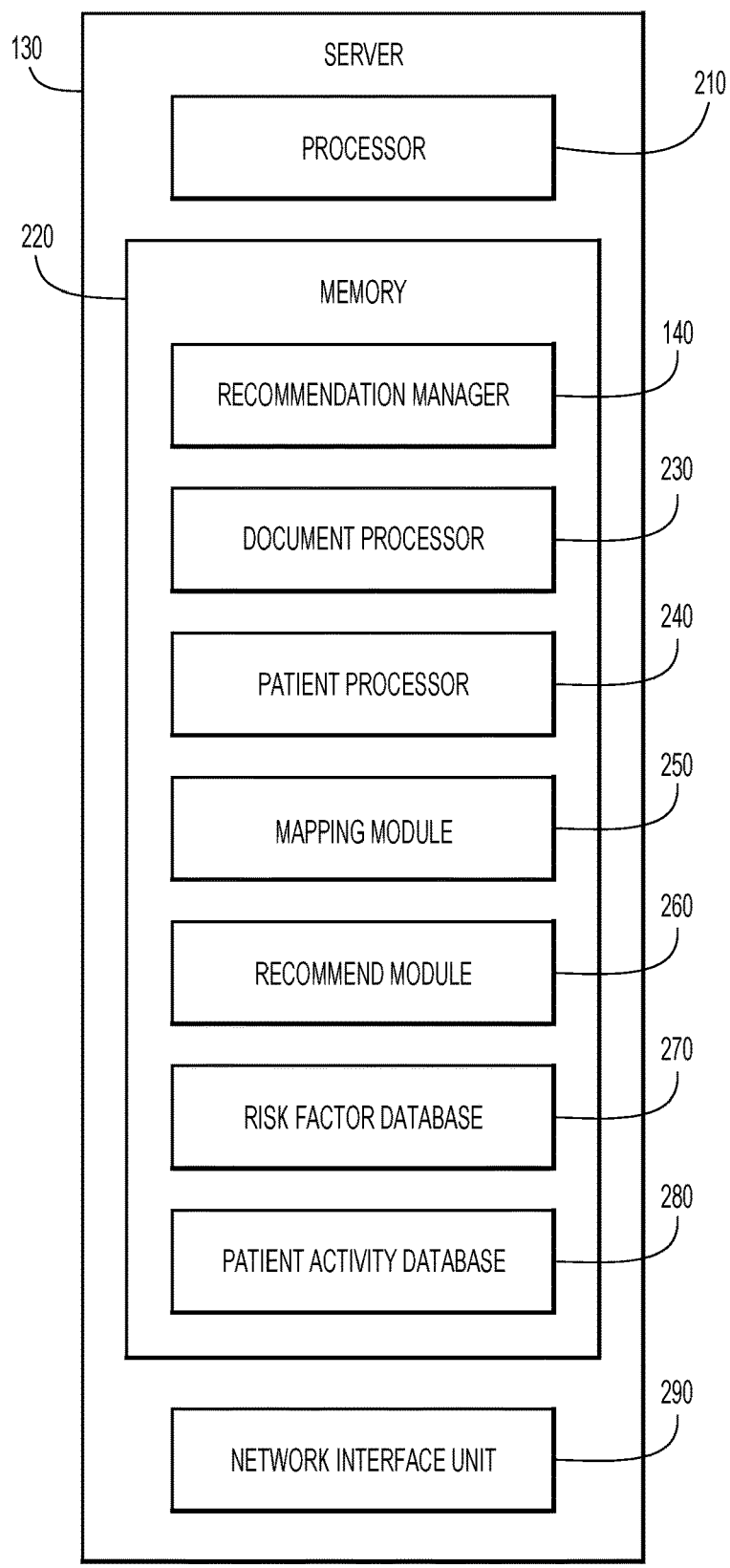
FIG. 2 is a block diagram illustrating a server of FIG. 1 in more detail according to an embodiment of the present invention.

Reference is now made to FIG. 2, which shows an example block diagram of a server 130 configured for generating medical screening recommendations based on patient activity information according to present invention embodiments. It should be understood that there are numerous possible configurations for server 130, and FIG. 2 is meant to be an example of one of the possible configurations. Server 130 includes a processor 210, a memory 220, and a network interface unit 290. The network interface (I/F) unit (NIU) 290 is, for example, an Ethernet card or other interface device that allows the server 130 to communicate over communication network 160. Network I/F unit 290 may include wired and/or wireless connection capabilities.

Processor 210 may include a collection of microcontrollers and/or microprocessors, for example, each configured to execute respective software instructions stored in the memory 220. Portions of memory 220 (and the instructions therein) may be integrated with processor 210.

Memory 220 may comprise read only memory (ROM), random access memory (RAM), magnetic disk storage media devices, optical storage media devices, flash memory devices, electrical, optical, or other physical/tangible (e.g., non-transitory) memory storage devices. Thus, in general, memory 220 may comprise one or more computer readable storage media (e.g., a memory device, etc.) encoded with software comprising computer executable instructions and when the software is executed (e.g., by processor 210) it is operable to perform the operations described herein. For example, memory 220 stores or is encoded with instructions or modules for recommendation manager 140, which is configured to generate one or more recommendations for medical screenings related to one or more medical conditions based on patient activity information. Optionally, user device 110 and/or server 130 may, individually or in combination, include recommendation manager 140 to perform the medical screening recommendations based on patient activity information.

Memory 220 may further store or is encoded with instructions for recommendation manager 140 to perform overall control of the recommendation operations described herein by analyzing patient electronic medical record (EMR) and social media information to generate recommendations for one or more medical tests (e.g., medical lab or other tests, medical or other procedures, etc.) based on patient activity indicated in the EMR and social media information. Recommendation manager 140 may include or interact with multiple components, including document processor 230, patient processor 240, mapping module 250, recommend module 260, risk factor database 270, and patient activity database 280. Recommendation manager 140 is further configured to receive one or more requests from user device 110 to recommend one or more medical screenings and, in response, send one or more recommendations for one or more medical tests (e.g., medical lab or other tests, medical or other procedures, etc.) to user device 110 for display to a user associated with user device 110 (e.g., medical service provider, insurance representative, etc.) on a user interface of display 120. Recommendation manager 140 is further configured to store the one or more recommendations for medical screenings based on patient activity information in patient activity database 280 for further recommendation operations.

Document processor 230 may be configured to retrieve and analyze a collection of medical and/or other documents to identify one or more risk factors (or activities) associated with one or more medical conditions. A machine learning model is trained to map the risk factors (or activities) to medical tests associated with the one or more medical conditions.

Patient processor 240 may be configured to analyze a patient electronic medical record (EMR) and mine social media data associated with the patient to identify one or more risk factors (or activities) in which the patient may be engaged.

Mapping module 250 may be configured to generate, train, and apply a machine learning model to map one or more patient risk factors (or activities) to one or more medical tests (e.g., medical lab or other tests, medical or other procedures, etc.). According to an embodiment of the present invention, mapping module 250 may generate a confidence score associated with the risk factors and medical tests.

Recommend module 260 may be configured to filter the medical tests produced by the model (or mapping module 250), and generate a recommendation including one or more medical tests for a patient based on associated confidence scores for the medical tests. Recommend module 260 may further filter the medical tests based on prior performance and physician feedback.

Recommendation manager 140, document processor 230, patient processor 240, mapping module 250, and recommend module 260 may include one or more modules or units to perform the various functions of present invention embodiments described below. The various modules (e.g., recommendation manager, document processor, patient processor, mapping module, recommend module, etc.) may be implemented by any combination of any quantity of software and/or hardware modules or units, and may reside within memory 220 of server 130 for execution by processor 210.

Memory 220 may further provide risk factor database 270, which stores various information related to a plurality of risk factors (or activities) identified within the text of a collection of documents. Similarly, patient activity database 280 may store risk factors (or activities) associated with a given patient based on the patient activities (e.g., in an electronic medical record (EMR), in social media data, etc.). Risk factor database 270 and patient activity database 280 may be implemented by any conventional or other database or storage unit, may be local to or remote from server 130, and may communicate via any appropriate communication medium (e.g., local area network (LAN), wide area network (WAN), Internet, hardwire, wireless link, Intranet, etc.).

Servers 130 may be implemented by any conventional or other computer systems preferably equipped with a display or monitor, a base (e.g., including at least one processor 210, one or more memories 220 and/or internal or external network interfaces or communications devices 290 (e.g., modem, network cards, etc.), optional input devices (e.g., a keyboard, mouse or other input device), and any commercially available and custom software (e.g., server/communications software, recommendation manager, etc.).

Figure 3:
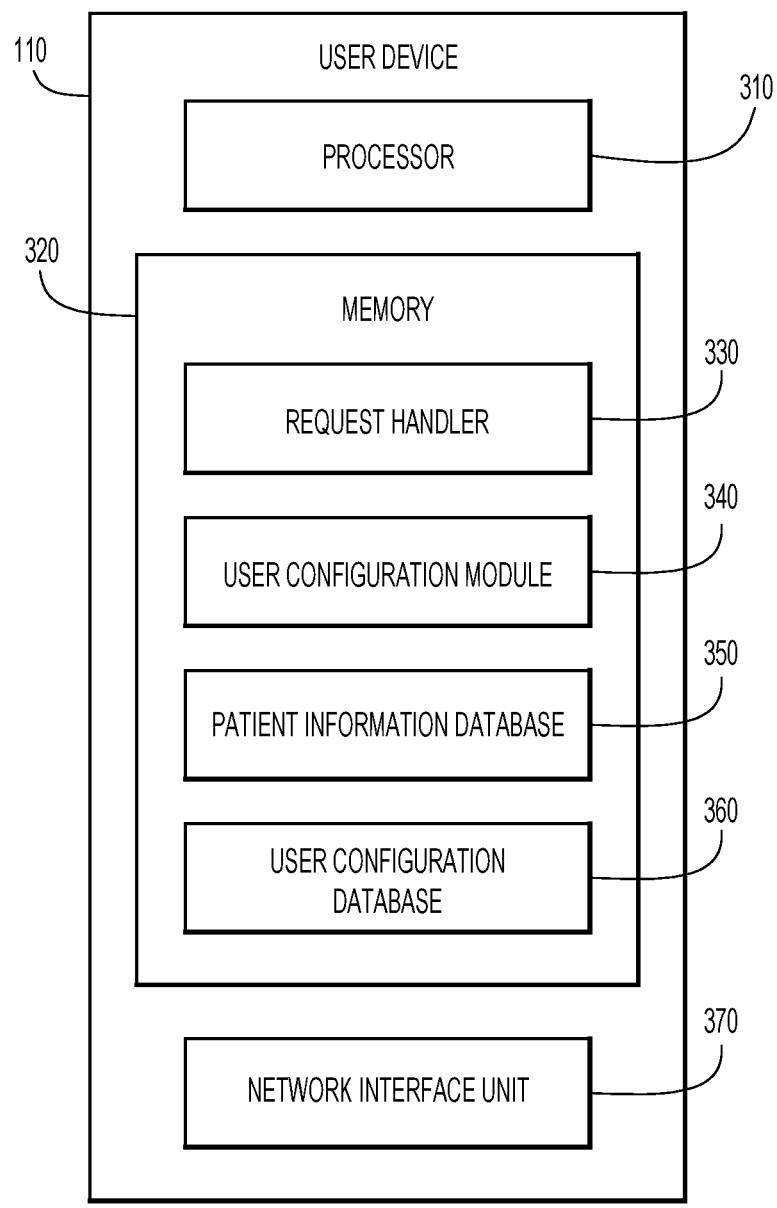
FIG. 3 is a block diagram illustrating a user device of FIG. 1 in more detail according to an embodiment of the present invention.

Reference is now made to FIG. 3, which shows an example block diagram of a user device 110 configured to request and receive one or more medical screening recommendations according to present invention embodiments. It should be understood that there are numerous possible configurations for user device 110, and FIG. 3 is meant to be an example of one of the possible configurations. User device 110 includes a processor 310, a memory 320, and a network interface unit 370. The network interface (I/F) unit (NIU) 370 is, for example, an Ethernet card or other interface device that allows user device 110 to communicate over communication network 160. Network I/F unit 370 may include wired and/or wireless connection capabilities.

Processor 310 may include a collection of microcontrollers and/or microprocessors, for example, each configured to execute respective software instructions stored in the memory 320. Memory 320 may include various modules for execution by processor 310, including request handler 330 and user configuration module 340. Memory 320 may further include patient information database 350 and user configuration database 360. Portions of memory 320 (and the instructions or modules therein) may be integrated with processor 310.

Memory 320 may comprise read only memory (ROM), random access memory (RAM), magnetic disk storage media devices, optical storage media devices, flash memory devices, electrical, optical, or other physical/tangible (e.g., non-transitory) memory storage devices. Thus, in general, memory 320 may comprise one or more computer readable storage media (e.g., a memory device, etc.) encoded with software comprising computer executable instructions and when the software is executed (e.g., by processor 310) it is operable to perform the operations described herein. For example, memory 320 stores or is encoded with instructions for request handler 330 to perform overall control of the requesting, receiving and displaying operations of the medical screening recommendations based on patient activities by receiving one or more inputs from multiple components, including user configuration module 340, patient information database 350, and user configuration database 360. Request handler 330 is further configured to send one or more requests for medical screening recommendations, and information associated with one or more patients, to recommendation manager 140 to determine, based on the received information associated with the one or more patients, recommendations for one or more medical tests (e.g., medical lab or other tests, medical or other procedures, etc.) for display on user device 110.

User configuration module 340 is configured to allow a user to set one or more parameters and/or user preferences associated with the user and/or related to the display of recommendations for medical screenings on user device 110. Accordingly, user configuration module 340 allows a user to set security and/or display preference such that incoming recommendations are displayed in accordance with the user's preference. It should be understood that user configuration module 340 may use any input device and/or graphical user interface (GUI) to receive one or more parameters and/or user preferences from a user associated with user device 110.

Request handler 330 and user configuration module 340 may include one or more modules or units to perform the various functions of present invention embodiments described below. The various modules (e.g., request handler, user configuration module, etc.) may be implemented by any combination of any quantity of software and/or hardware modules or units, and may reside within memory 320 of user device 110 for execution by processor 310.

Patient information database 350 may store various information related to one or more patients, while user configuration database 360 may store various information used and generated by request handler 330 for requesting and displaying one or more medical screening recommendations on user device 110. For example, patient information database 350 may store electronic medical record (EMR) information associated with one or more patients, and user configuration database 360 may store one or more characteristics or preferences associated with a user of user device 110 (e.g., security preferences, display preferences, etc.). Patient information database 350 and user configuration database 360 may be implemented by any conventional or other database or storage unit, may be local to or remote from servers 130, and may communicate via any appropriate communication medium (e.g., local area network (LAN), wide area network (WAN), Internet, hardwire, wireless link, Intranet, etc.).

User devices 110 may be implemented by any conventional or other computer systems preferably equipped with a display or monitor, a base (e.g., including at least one processor 310, one or more memories 320 and/or internal or external network interfaces or communications devices 370 (e.g., modem, network cards, etc.), optional input devices (e.g., a keyboard, mouse or other input device), and any commercially available and custom software (e.g., browser/communications software, request handler, user configuration module, etc.).

Figure 4:
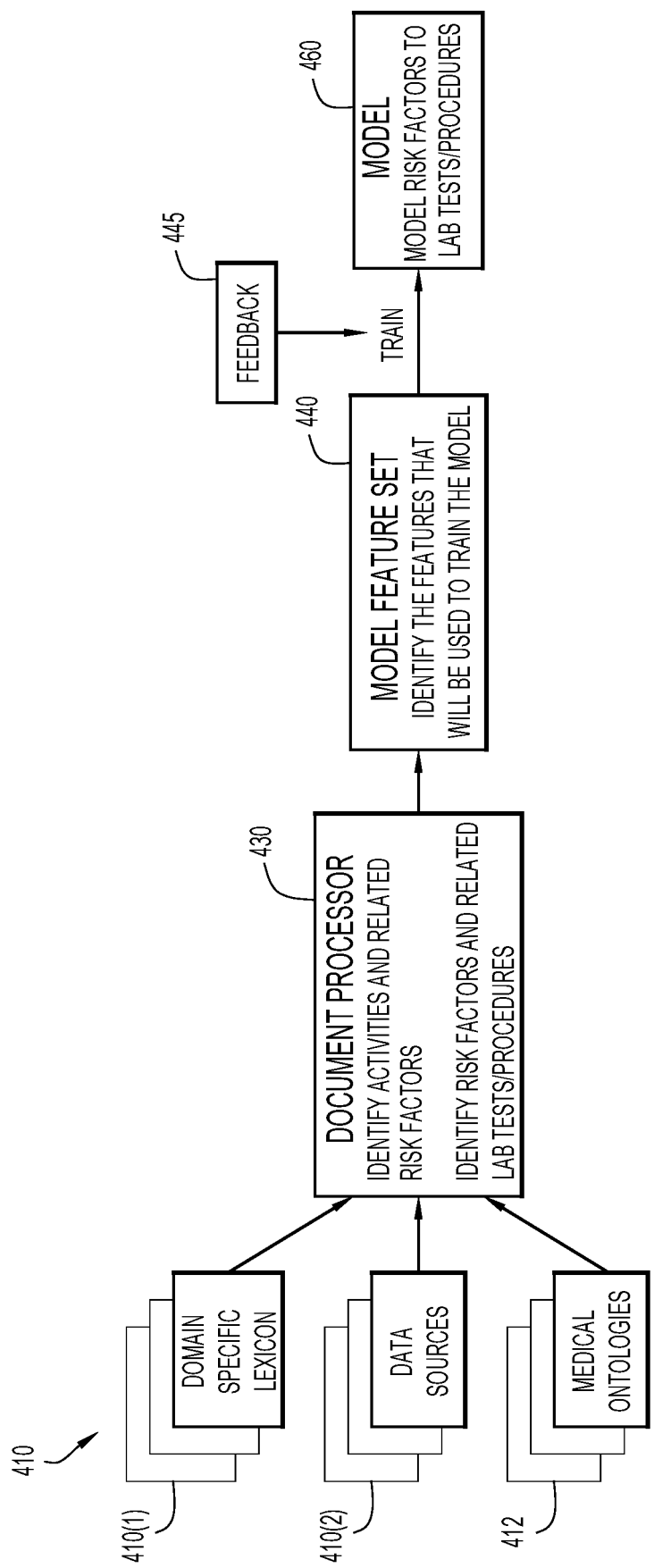
FIG. 4 is a flow diagram for analyzing medical documents and training a model to map risk factors of medical conditions to medical tests based on patient activity according to an embodiment of the present invention.

Present invention embodiments employ machine learning to generate and train a model to provide mappings between risk factors (or activities) and corresponding medical screenings or tests (e.g., medical lab or other tests, medical or other procedures, etc.). The model may be utilized to recommend medical tests based on patient activities discovered within electronic medical records (EMR), social media data, or other sources of patient information. A manner of generating and training a model (e.g., via one or more servers 130) to map risk factors (or activities) to medical tests (e.g., medical lab or other tests, medical or other procedures, etc.) is illustrated in FIG. 4. Initially, document processor 230 receives and analyzes various documents 410 from document repositories 150 at flow 430. The documents may include domain specific lexicons or dictionary 410(1) and medical or other documents 410(2) from various sources (e.g., documents from Elsevier, Dynamed, Merek Manual, PubMed, Center for Disease Control (CDC), National Institute of Health (NIH), etc.).

In addition, document processor 230 may receive various medical ontologies 412 (e.g., Unified Medical Language System (UMLS), etc.) providing hierarchies and relationships of medical concepts (e.g., medical conditions, corresponding medical lab or other tests, medical or other procedures, etc.).

Document processor 230 analyzes documents 410(2), terms in domain specific dictionary 410(1), and data provided by the various medical ontologies 412 (UMLS, etc.) to identify concepts and relationships within the documents. The analysis may utilize various Natural Language processing (NLP) techniques (e.g., semantic analysis, query expansion, concept/entity detection, relationship detection, temporal analysis, negation, etc.). The document processor may employ or include a cognitive medical system (e.g., an IBM Watson Health pipeline, IBM Watson Concept Insights, etc.) to perform these NLP techniques.

For example, semantic analysis may be used to identify a grammatical structure of document text, thereby enabling understanding of all possible interpretations of a given text string. Query expansion may be employed to expand individual terms within the document into their various surface forms.

Concept/Entity detection may be used to identify entities (e.g., people, doctors, organizations, etc.) and relevant concepts of the medical ontology within the document text (e.g., based on the text and corresponding expansions). The scope of complexity may vary from identifying a medical concept expressed in the text (e.g., the word "hypertension") to inferring the medical concept (e.g., from the phrase "Elevated Blood Lead Level"). Concept detection uses the domain specific lexicons and key phrases identified from the documents. Some of the lexicons may also be provided by the medical ontologies. In addition, concept detection may be utilized to identify risk factors (or activities) within the documents. These risk factors (or activities) may be concepts within other ontologies (e.g., hobby ontology, occupation/profession ontology, etc.).

Relationship detection identifies relationships between the identified concepts/entities. For example, "elevated blood lead level" may have a relationship of "caused by" to a medical concept of "exposure to lead."

A knowledge graph can be used as part of query expansion to identify related or similar concepts, and a closeness (e.g., distance, etc.) or strength of the relationship between the identified concepts. By way of example, a medical concept of "hypertension" may be directly related to a medical concept of "heart disease", and a medical concept of "ACEI Inhibitor" may be directly related to the medical concept of "hypertension". A distance score within a medical ontology may be determined between these concepts to indicate a strength of the relationship (e.g., a distance of one hop may be between "heart disease" and "hypertension", while a distance of two hops may be between "heart disease" and "ACEI Inhibitor" (through the direct relation of "ACEI Inhibitor" to "hypertension")). Further, an occupation concept/risk factor of "Police Protection" may be determined to be similar to concepts/risk factors of "Military", "Police", "State Trooper", "Mall Cop", "SWAT", etc.

Temporal analysis identifies date and/or time references within the documents, and allows association with concepts. These references may be combined with dates provided in electronic medical records (EMR) and/or other sources of information. By way of example, a clinical note created on a certain date, with the text "Exposed to lead 3 weeks ago", enables a determination that the exposure occurred around a certain prior date.

Negation identifies text where a concept is negated. For example, "Patient had no exposure to lead last year," where "exposure to lead" is a medical concept, and "last year" is temporal and indicates when the patient had lead exposure. Negation recognizes the word "no" and given the context, negates the medical concept to indicate there was no exposure at that time.

The Natural Language Processing (NLP) techniques are utilized to identify medical concepts of the medical ontologies within medical documents 410(2). Once the medical concepts are identified, the sections of the medical documents containing those medical concepts are analyzed by the NLP techniques to identify risk factors (or activities) associated with the medical concepts. In addition, the document sections and/or medical ontologies may be further analyzed to identify medical tests (e.g., medical lab or other tests, medical or other procedures, etc.) associated with the identified medical concepts. The medical tests may be ascertained from the document sections containing the medical concepts, be included within, and/or associated with medical concepts of, the medical ontologies, and/or have pre-defined associations with medical conditions and/or medical concepts.

Since the risk factors (or activities) and medical tests are each associated with corresponding medical concepts, a mapping may be determined between the risk factors (or activities) and medical tests based on their associations to the medical concepts. For example, a document may indicate that people in certain occupations involving firearms (e.g., employees of ranges, military, police protection, etc.) have elevated blood lead levels. The NLP techniques may identify blood lead levels as the medical concept, elevated as a modifier, people as an entity, and the certain occupations as related to the medical concept. A model may be trained to associate medical tests for blood lead levels based on the patient occupations.

The results of the Natural Language Processing (NLP) techniques include the identified medical concepts, identified risk factors (or activities), and corresponding relationships. These results are analyzed by the document processor to identify features (e.g., risk factors/activities) for a feature set that is used to train the model to produce the mappings between the risk factors (or activities) and medical tests at flow 440. The feature set includes for one or more medical concepts (and associated medical tests) one or more risk factors (or activities) associated with the medical concept. The document processor may utilize various criteria to determine whether to include a risk factor (or activity) for a given medical concept (and associated medical test) within the feature set (e.g., strength of the relationship with the medical concept, distances of the risk factor or associated medical concept within one or more ontologies, frequency of occurrence of the risk factor (or activity) in the medical documents, etc.). A feature score or weighted feature score may be determined based on the criteria and compared to a feature threshold to determine whether to include a feature in the feature set.

The document processor is in essence analyzing the documents to identify features that may be used to train the model to associate or map medical tests to patient activities indicated in sources of patient information (e.g., indicated within electronic or other medical records, social media data, etc.). Referring to the above example of elevated blood lead levels, identified features (e.g., risk factors/activities) may include "Profession: Police Protection," "Hobby: Target Shooting," etc. These identified features may be used to train the model to map the features (e.g., risk factors/activities) to medical tests. These features may further be expanded via query expansion as described above. For example, features similar to Police Protection may be determined to include "Military," "Police," "State Trooper," "Mall Cop," "SWAT," etc. The expanded features may be included in the feature set to train the model. Patient processor 240 analyzes patient information (e.g., social media posts, social media profiles, a patient electronic medical record, etc.) for the features in the feature set, and provides results of the analysis to the trained model to recommend medical tests for a patient.

Once the feature set for the model is identified, mapping module 250 generates and trains the model at flow 460 to map the feature set (e.g., of risk factors/activities) to medical tests. An example mapping of risk factors (or activities) to medical tests by the model is illustrated in FIG. 5. By way of example, the mappings are shown in the form of a table 500, but any suitable data or other structure may be utilized. The table includes columns for the risk factors (or activities) (e.g., Risk Factor 1, Risk Factor 2, Risk Factor 3, and Risk Factor 4 as viewed in FIG. 5) and the medical tests (e.g., Lab Test/Procedure as viewed in FIG. 5), where each table row 510, 520, 530 indicates a set or combination of the risk factors (or activities) mapped to the corresponding medical test. In this example, the values of 1 and 0 are used to respectively indicate the presence and absence of a risk factor for a corresponding medical test (e.g., a combination of Risk Factor 1 and Risk Factor 2 are mapped to a Lab Test/Procedure indicated by a medical or other code or identifier of TEST 1; a combination of Risk Factor 2 and Risk Factor 3 are mapped to a Lab Test/Procedure indicated by a medical or other code or identifier of TEST 2; a combination of Risk Factor 2 and Risk Factor 4 are mapped to a Lab Test/Procedure indicated by a medical or other code or identifier of TEST 2; etc.). However, the values may be any values, and the combinations may include any quantity of any risk factors (or activities) and may map to the same or different medical tests.

When the model is trained, weights are calculated and applied to each risk factor (or activity). For example, a pregnancy test may apply a very high weight to a feature of "female". Further, the weights may be based on the corresponding feature scores (or weighted feature scores) and/or various other criteria (e.g., strength of the relationship with the corresponding medical concept, distances of the risk factor or associated medical concept within one or more ontologies, frequency of occurrence of the risk factor (or activity) in the medical documents, etc.). The weights may be of any values, and combined in any fashion (e.g., summed, multiplied, applied to values of the risk factor, etc.) to produce a medical test score that may be used (e.g., compared to a threshold, compared to scores of other lab tests/procedures, etc.) to determine the appropriate medical tests. For example, a medical test may not be recommended for a patient having only low weight risk factors for the medical test.

Further, the model may receive confidence scores associated with risk factors based on mining the patient electronic medical record (EMR) information and social media data. The confidence scores may be based on various criteria (e.g., quantity of references to the risk factor, the distance from the medical concepts in the medical ontology associated with the risk factor identified in the EMR and social media data to the original medical concepts identifying the procedures, etc.). Various confidence scores for the risk factors may be used in the model during training to adjust the weights of the risk factors and/or medical test scores.

The model may be implemented by any conventional or other machine learning models (e.g., neural networks, rule-based models, mathematical/probabilistic models, K-Nearest Neighbor model, Singular Value Decomposition (SVD) model, naive Bayes classifiers, etc.). The models preferably employ supervised learning/training techniques, but any suitable learning/training techniques may be employed. The model may be trained to distinguish between a plurality of medical tests for a set of risk factors (or activities). For example, a training set may be established by subject matter experts (e.g., a set of risk factors/medical conditions and corresponding desired medical tests), and the model may be trained on the training set to learn these mappings. The medical test scores (e.g., based on the weights of the risk factors) may be compared to a medical test threshold (e.g., score value, etc.) to narrow results to a preferred set of medical tests appropriate for the risk factors.

The models may provide a confidence score with the determined medical tests. For example, the weights and/or confidence scores assigned to the risk factors (or activities) may be combined in any fashion (e.g., summed, multiplied, applied to values of the risk factor, etc.) to produce a confidence score for the determined medical tests (e.g., medical lab or other tests, medical or other procedures, etc.). The type of model employed may provide a confidence score for the medical tests based on model training. For example, a K-nearest neighbor model may provide K medical tests (e.g., where K may be provided by a user, etc.) based on highest probabilities for those medical tests generated from training the model.

In addition, feedback may be provided in response to the medical tests produced by the model, and used for adaptive training at flow 445. For example, a physician or other medical service provider may change (or recommend different medical tests than) the medical tests produced by the model for a patient with certain risk factors. The changed medical tests may be used (e.g., in a training set, etc.) to re-train the model (e.g., determine new weights, determine new mappings between risk factors and medical tests, etc.). Further, documents 410 may be updated with new documents that should be considered for training. In this case, accuracy of the model may be measured with the new documents (e.g., with respect to a training set), and the model re-trained when the accuracy level falls below a desired threshold (e.g., accuracy on the training set falls below a certain percentage, etc.). Thus, the model may be constantly trained based on feedback and/or new documents provided to the document repositories.

Figure 6:
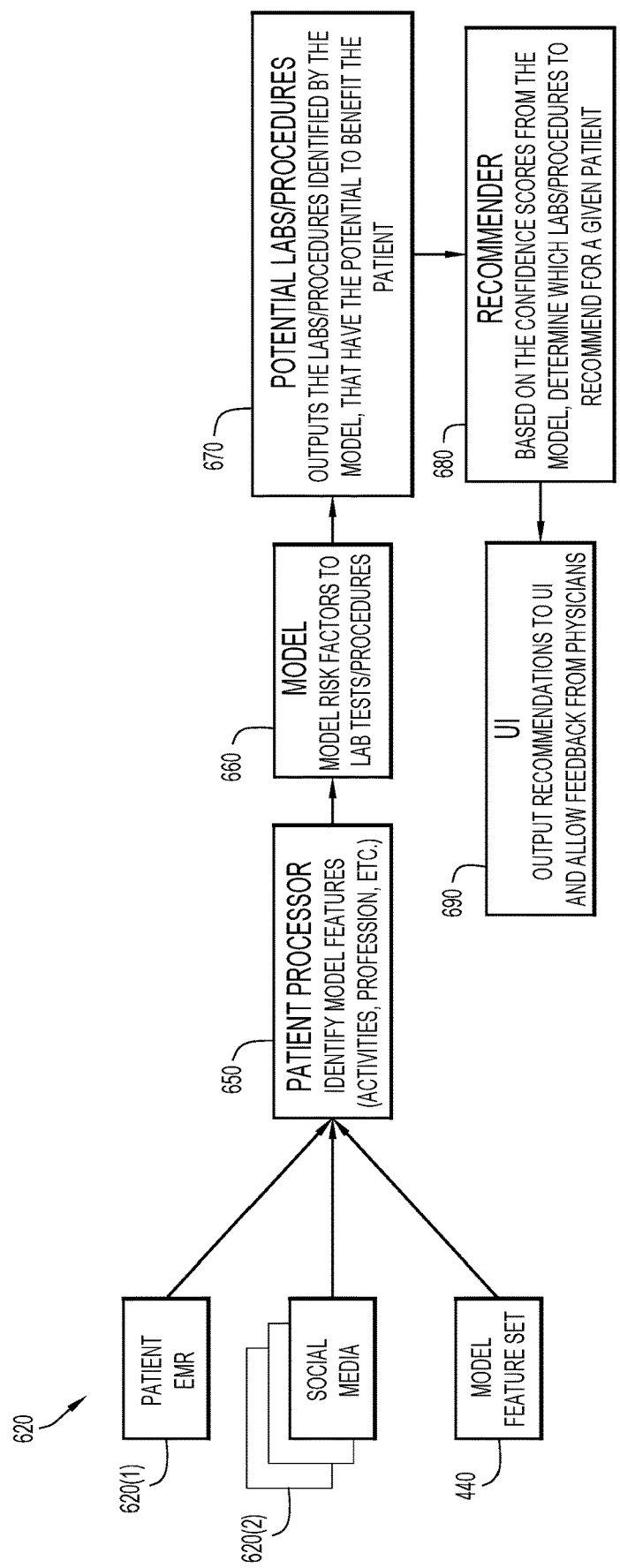
FIG. 6 is a diagrammatic illustration of analyzing patient activity for risk factors of medical conditions and recommending medical tests according to an embodiment of the present invention.

Once the model is trained, the model may be utilized to determine medical tests (e.g., medical lab or other tests, medical or other procedures, etc.) based on risk factors (or activities) within patient information (e.g., electronic medical records (EMR), social media data, etc.) as illustrated in FIG. 6. Initially, patient processor 240 receives and analyzes patient information 620 from various data sources (e.g., electronic medical records (EMR) 620(1), social media information from social media networks 620(2), etc.) at flow 650. The patient information may include information concerning participation of a patient in various activities (or risk factors). In addition, patient processor 240 may receive model feature set 440 (e.g., the features (or risk factors/activities) the model has been trained to map to medical tests as described above).

Patient processor 240 analyzes the patient information (e.g., using the set of Natural Language Processing (NLP) techniques described above) to identify the risk factors (or activities) of model feature set 440 (e.g., hobby, profession/occupation, etc.) present in the patient information (e.g., electronic medical record (EMR) (e.g., structured and/or unstructured information, etc.), social media data (e.g., profiles, posts, etc.), etc.). Each risk factor may be associated with a confidence score determined based on various criteria (e.g., quantity of references to the risk factor, the distance from the medical concepts in the medical ontology associated with the risk factor identified in the EMR and social media data to the original medical concepts identifying the medical tests, etc.). The identified risk factors (or activities) of the feature set from the patient information are provided to mapping module 250 at flow 660 to apply those risk factors to the trained model. The model maps the identified risk factors (or activities) to medical tests (e.g., medical lab or other tests, medical or other procedures, etc.), and provides a list of corresponding medical tests that may be applicable to, and/or have the potential to benefit, the patient at flow 670. The confidence scores of the identified risk factors may further be supplied to the model to produce the corresponding medical tests (e.g., where various confidence scores for the risk factors may be used by the model during training to adjust the weights of the risk factors and/or medical test scores, etc.). Each medical test may be associated with a confidence score indicating the likelihood that the result is relevant to the patient based on the input risk factors (or activities) to the model. The confidence score for the test may be based on various criteria (e.g., weights assigned to the risk factors within the model, confidence score of the risk factors, medical test scores, confidence score generated based on model training, etc.).

Recommend module 260 receives the medical tests provided by the model, and filters the results to provide a preferred or recommended set of medical tests for the patient to a user interface of display 120 at flow 680. For example, the confidence scores of the medical tests provided by the model may be compared to a confidence cut-off or threshold score, where each result with a confidence score greater than the threshold (e.g., percentage of confidence (e.g., 90%, 80%, etc.)) is provided to the user interface. The recommend module may also determine which medical tests have been previously conducted for the patient to avoid recommending medical tests already performed. Moreover, the recommend module may perform validation to avoid recommending the same medical test plural times. In addition, the recommend module may manage physician or other medical service provider feedback for a given patient to avoid recommending medical tests the physician has indicated the patient does not need.

The recommend module may also provide evidence supporting the recommended medical tests. The evidence may include the identified risk factors from patient electronic medical records (EMR) and social media data, the confidence level of each identified risk factor and/or medical test, and the data from which the risk factors are derived. In addition, evidence supporting the association of the medical tests with the risk factors may be provided (e.g., excerpts from medical documents, etc.).

The recommended medical tests are provided by a user interface on display 120 of user device 110 at flow 690. The user interface may further receive feedback from a physician or other medical service provider that may be used for training the model as described above. The feedback may be used in training to adjust the weights associated with risk factors in the model and improve the model accuracy over time.

Operation of an embodiment of the present invention is described with respect to an example scenario. Initially, a corpus of medical documents is analyzed to understand a connection between various medical tests (e.g., medical lab or other tests, medical or other procedures, etc.) and risk factors (or activities) that may cause those medical tests to be performed. The corpus of medical documents may include a myriad of medical content from various sources (e.g., documents from Elsevier, Dynamed, Merek Manual, PubMed, Center for Disease Control (CDC), etc.).

By way of example, a report from an authority (e.g., CDC, etc.) pertaining to indoor firing ranges may describe associations between activities and blood lead levels. Based on analysis of the document (e.g., utilizing NLP techniques as described above), the following information may be deduced: Employees, their families and customers of Indoor Firing Ranges are at risk of elevated blood lead levels; People involved in police protection are at risk of elevated blood lead levels; and people who are involved in target shooting are at risk of elevated blood lead levels. Individuals participating in these risk factors may not be aware of the risk to lead exposure, and may never inform their physician of these activities.

An elevated blood lead level is a medical concept of a medical ontology which can be processed by server 130 and mapped to potential medical tests (e.g., medical lab or other tests, medical or other procedures, etc.) via a machine learning model. For example, SNOMED provides two potential procedures for blood lead levels which can be mapped to the risk factors (e.g., Employment: Indoor Firing Range; Employment: Police Protection; Hobby: Target Shooting).

These risk factors (or activities) may be expanded (e.g., via query expansion) to other similar activities. For example, features similar to Police Protection may include "Military," "Police," "State Trooper," "Mall Cop," "SWAT," etc. Thus, the table of risk factors may be expanded to many possible identifiable features in a patient's electronic medical record (EMR) or their social media data (e.g., social media posts or communications, social media profiles, etc.).

When a patient visits a physician or other medical service provider, the patient electronic medical record (EMR) and social media data may be analyzed to identify these potential risk factors. The patient EMR (e.g., from structured fields and/or unstructured fields (e.g., doctors notes, etc.)) may provide occupational and other information to determine participation in risk factors (e.g., Police Protection, etc.). Social media data may similarly provide activities of the patient pertaining to the risk factors. A confidence score for particular risk factors may be produced based on the risk factors identified in the EMR and social media data and various criteria (e.g., quantity of references to the risk factor, the distance from the medical concepts in the medical ontology associated with the risk factors identified in the EMR and social media data to the original medical concepts identifying the medical tests, etc.).

The model processes the risk factors of the patient identified from the electronic medical record (EMR) and/or social media data (e.g., and corresponding risk factor confidence scores), and corresponding medical tests are recommended (e.g., based on the confidence scores from the model) that are potentially pertinent for the patient (e.g., a lead screening test, etc.).

The recommendation of the medical tests may also include evidence supporting the recommendation. The evidence may include the risk factors identified, the confidence level of each risk factor and/or medical test, and the data from which the risk factors are derived. In addition, evidence supporting the association of the medical tests with the risk factors may be provided (e.g., excerpts from medical documents, etc.).

The physician or other medical service provider may readily understand that the medical tests being recommended are based on the patient being exposed to an indoor firing range, and that the reporting authority indicates exposure to an indoor firing range may cause elevated blood lead levels. The physician may ask the patient about their exposure, and potentially order the lead blood screening from the system.

Alternatively, the system may automatically generate communications and transmit them to corresponding facilities to arrange or schedule the screening, or generate and send controls (e.g., including medical and other parameters, etc.) to medical devices to perform the screening (e.g., x-ray or other scanning device, etc.).

Advantages of the present invention embodiments include dynamically recommending one or more medical tests (e.g., medical lab or other tests, medical or other procedures, etc.) that may be related to one or more risk factors associated with activities indicated in a patient's electronic medical record (EMR) and/or social media data. Furthermore, because the system may efficiently review and analyze current medical documents and patient EMR, the system significantly improves the determination of the medical tests that are most likely to be related to a patient's activities, avoiding the expense and inconvenience of performing unnecessary and/or duplicative procedures and/or tests.

It will be appreciated that the embodiments described above and illustrated in the drawings represent only a few of the many ways of implementing machine learning for medical screening recommendations based on patient activity information in social media.

The environment of the present invention embodiments may include any number of computer or other processing systems (e.g., user devices, server systems, etc.) and databases or other repositories arranged in any desired fashion, where the present invention embodiments may be applied to any desired type of computing environment (e.g., cloud computing, client-server, network computing, mainframe, stand-alone systems, etc.).

The computer or other processing systems employed by the present invention embodiments may be implemented by any number of any personal or other type of computer or processing system (e.g., desktop, laptop, PDA, mobile devices, etc.), and may include any commercially available operating system and any combination of commercially available and custom software (e.g., recommendation manager, document processor, patient processor, mapping module, recommend module, etc.). These systems may include any types of monitors and input devices (e.g., keyboard, mouse, voice recognition, etc.) to enter and/or view information.

It is to be understood that the software (e.g., recommendation manager, document processor, patient processor, mapping module, and recommend module, etc.) of the present invention embodiments may be implemented in any desired computer language and could be developed by one of ordinary skill in the computer arts based on the functional descriptions contained in the specification and flow charts illustrated in the drawings. Further, any references herein of software performing various functions generally refer to computer systems or processors performing those functions under software control. The computer systems of the present invention embodiments may alternatively be implemented by any type of hardware and/or other processing circuitry.

The various functions of the computer or other processing systems may be distributed in any manner among any number of software and/or hardware modules or units, processing or computer systems and/or circuitry, where the computer or processing systems may be disposed locally or remotely of each other and communicate via any suitable communications medium (e.g., LAN, WAN, Intranet, Internet, hardwire, modem connection, wireless, etc.). For example, the functions of the present invention embodiments may be distributed in any manner among the various user devices and server systems, and/or any other intermediary processing devices. The software and/or algorithms described above and illustrated in the flow diagrams may be modified in any manner that accomplishes the functions described herein. In addition, the functions in the flow diagrams or description may be performed in any order that accomplishes a desired operation.

The software of the present invention embodiments (e.g., recommendation manager, document processor, patient processor, mapping module, recommend module, etc.) may be available on a non-transitory computer useable medium (e.g., magnetic or optical mediums, magneto-optic mediums, floppy diskettes, CD-ROM, DVD, memory devices, etc.) of a stationary or portable program product apparatus or device for use with stand-alone systems or systems connected by a network or other communications medium.

The communication network may be implemented by any number of any type of communications network (e.g., LAN, WAN, Internet, Intranet, VPN, etc.). The computer or other processing systems of the present invention embodiments may include any conventional or other communications devices to communicate over the network via any conventional or other protocols. The computer or other processing systems may utilize any type of connection (e.g., wired, wireless, etc.) for access to the network. Local communication media may be implemented by any suitable communication media (e.g., local area network (LAN), hardwire, wireless link, Intranet, etc.).

The system may employ any number of any conventional or other databases, data stores or storage structures (e.g., files, databases, data structures, data or other repositories, etc.) to store information (e.g., EMRs, social media data, risk factors, ontologies, dictionaries, relationships, etc.). The database systems may be implemented by any number of any conventional or other databases, data stores or storage structures (e.g., files, databases, data structures, data or other repositories, etc.) to store information. The database systems may be included within or coupled to the server and/or user devices. The database systems and/or storage structures may be remote from or local to the computer or other processing systems, and may store any desired data (e.g., EMRs, social media data, risk factors, ontologies, dictionaries, relationships, etc.).

The present invention embodiments may employ any number of any type of user interface (e.g., Graphical User Interface (GUI), command-line, prompt, etc.) for obtaining or providing information (e.g., patient activity, EMR, etc.), where the interface may include any information arranged in any fashion. The interface may include any number of any types of input or actuation mechanisms (e.g., buttons, icons, fields, boxes, links, etc.) disposed at any locations to enter/display information and initiate desired actions via any suitable input devices (e.g., mouse, keyboard, etc.). The interface screens may include any suitable actuators (e.g., links, tabs, etc.) to navigate between the screens in any fashion. Reports produced by the system may include any information arranged in any fashion, and may be configurable based on rules or other criteria to provide desired information to a user (e.g., medical screening recommendations, risk factor analysis, etc.).

The present invention embodiments are not limited to the specific tasks or algorithms described above, but may be utilized for any type of candidate subjects (e.g., persons, animals, etc.) to perform any type of health-related recommendations based on any type of physical or other activities (e.g., personal, business, hobby, sports, common tasks, habits, profession/occupation, eating, sleeping, illnesses, etc.). Any type of medical or other test or action may be recommended (e.g., medical procedure, examination, diagnostic screening (e.g., x-ray, MRI, CT Scan, ultrasound, etc.)) for any medical conditions. Any type of machine learning or model may be employed to map activities to any medical or other tests. The weights, confidence and other scores, and thresholds or cut-offs may be set to any desired values in any value ranges. The risk factors may be of any quantity, and include any desired activities (e.g., sport, hobby, common tasks, etc.). Any type of medical or other documents may be analyzed to determine relationships between the activities and medical or other tests, procedures, or courses of action. Further, any information associated with a patient or other entity may utilized to determine participation in activities or risk factors (e.g., social media data of the patient, social media or other data of any of the patients contacts or other entities referencing the patient, medical or other records, etc.).

The system may perform any desired actions in response to the recommendations to commence the medical tests. For example, the system may create and transmit notifications to corresponding medical facilities (or medical service provider systems) to schedule and/or perform a recommended medical test. Further, the system may automatically generate controls and parameters (e.g., specific to the patient based on analysis of EMR data, etc.) in accordance with a recommended medical test, and/or control a corresponding medical device to perform the desired medical test (e.g., x-ray, scanner, blood pressure sensor, thermometer, cardiac or stress test, etc.).

Any type of machine learning or model may be employed to continuously and/or adaptively learn to produce new or modified recommendations based on feedback and/or updated or new information (e.g., documents, EMR, social media data, etc.). The feedback and/or new documents may be automatically fed into the system to dynamically update and re-train the model (e.g., for new or modified recommendations, etc.).

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises", "comprising", "includes", "including", "has", "have", "having", "with" and the like, when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

What is claimed is:

1. A method of analyzing patient activity to conduct appropriate medical tests comprising:
    analyzing, via at least one processor, a collection of medical documents employing natural language processing to identify within document content risk factors of medical conditions associated with corresponding activities;
    generating, via the at least one processor, feature sets of the identified risk factors for the medical conditions, wherein a feature is selected for a feature set in response to a feature score satisfying a threshold, and wherein the feature score is based on a distance within a medical ontology between the feature and a medical condition;
    expanding, via the at least one processor, the feature sets with at least one feature similar to a corresponding feature of the feature sets, wherein the corresponding feature includes one from a group of hobby related activities and occupational related activities, and wherein the similarity of the at least one feature is based on a distance within a first ontology from the corresponding feature;
    mapping, via the at least one processor, the identified risk factors of the activities to one or more medical tests for the associated medical conditions by training a machine learning model with the feature sets of the identified risk factors;
    analyzing, via the at least one processor, at least one data source about a patient to determine patient activities and generate a feature set for the patient based on the determined patient activities, wherein the at least one data source includes a social media network indicating the patient activities including one or more selected from a group of hobby related activities and occupational related activities; and
    determining, via the at least one processor, the one or more medical tests to conduct from the mapping based on the risk factors associated with the determined activities of the patient by:
        determining a confidence score for the risk factors associated with the determined activities of the patient;
        applying the feature set for the patient based on the determined patient activities and the confidence score for the risk factors associated with the determined activities of the patient to the machine learning model to provide the one or more medical tests to conduct;
        validating the one or more medical tests provided by the machine learning model against prior performance for the patient, prior recommendation to the patient, and prior feedback received from a medical service provider for the patient; and
        removing at least one medical test that failed the validation from the one or more medical tests provided by the machine learning model.

2. The method of claim 1, wherein the identified risk factors are concepts within a second ontology, and mapping the identified risk factors comprises:
   mapping concepts of the second ontology corresponding to the concepts of the identified risk factors to the one or more medical tests for the associated medical conditions.

3. The method of claim 1, wherein the confidence score is based on one or more from a group of: concepts of an ontology present in a medical record and social media communications, a quantity of references to the concepts in the medical record and social media communications, and a distance within the ontology between the concepts and medical concepts identifying the medical tests.

4. The method of claim 1, further comprising:
   providing evidence to support a determination of the one or more medical tests to conduct.

5. The method of claim 4, wherein the evidence includes one or more from a group of: the risk factors associated with the determined activities of the patient, and the confidence score for the risk factors associated with the determined activities of the patient.

6. The method of claim 1, wherein the at least one data source further includes medical records associated with the patient.

7. A system for analyzing patient activity to conduct appropriate medical tests comprising:
   at least one processor configured to:
      analyze a collection of medical documents employing natural language processing to identify within document content risk factors of medical conditions associated with corresponding activities;
      generate feature sets of the identified risk factors for the medical conditions, wherein a feature is selected for a feature set in response to a feature score satisfying a threshold, and wherein the feature score is based on a distance within a medical ontology between the feature and a medical condition;
      expand the feature sets with at least one feature similar to a corresponding feature of the feature sets, wherein the corresponding feature includes one from a group of hobby related activities and occupational related activities, and wherein the similarity of the at least one feature is based on a distance within a first ontology from the corresponding feature;
      map the identified risk factors of the activities to one or more medical tests for the associated medical conditions by training a machine learning model with the feature sets of the identified risk factors;
      analyze at least one data source about a patient to determine patient activities and generate a feature set for the patient based on the determined patient activities, wherein the at least one data source includes a social media network indicating the patient activities including one or more selected from a group of hobby related activities and occupational related activities; and
      determine the one or more medical tests to conduct from the mapping based on the risk factors associated with the determined activities of the patient by:
         determining a confidence score for the risk factors associated with the determined activities of the patient;
         applying the feature set for the patient based on the determined patient activities and the confidence score for the risk factors associated with the determined activities of the patient to the machine learning model to provide the one or more medical tests to conduct;
         validating the one or more medical tests provided by the machine learning model against prior performance for the patient, prior recommendation to the patient, and prior feedback received from a medical service provider for the patient; and
         removing at least one medical test that failed the validation from the one or more medical tests provided by the machine learning model.

8. The system of claim 7, wherein the identified risk factors are concepts within a second ontology, and mapping the identified risk factors comprises:
   mapping concepts of the second ontology corresponding to the concepts of the identified risk factors to the one or more medical tests for the associated medical conditions.

9. The system of claim 7, wherein the confidence score is based on one or more from a group of: concepts of an ontology present in a medical record and social media communications, a quantity of references to the concepts in the medical record and social media communications, and a distance within the ontology between the concepts and medical concepts identifying the medical tests.

10. The system of claim 7, wherein the at least one processor is further configured to:
    provide evidence to support a determination of the one or more medical tests to conduct.

11. The system of claim 10, wherein the evidence includes one or more from a group of: the risk factors associated with the determined activities of the patient, and the confidence score for the risk factors associated with the determined activities of the patient.

12. The system of claim 7, wherein the at least one data source further includes medical records associated with the patient.

13. A computer program product for analyzing patient activity to conduct appropriate medical tests comprising:
    one or more computer readable storage media collectively having program instructions embodied therewith, the program instructions executable by at least one processor to cause the at least one processor to:
       analyze a collection of medical documents employing natural language processing to identify within document content risk factors of medical conditions associated with corresponding activities;
       generate feature sets of the identified risk factors for the medical conditions, wherein a feature is selected for a feature set in response to a feature score satisfying a threshold, and wherein the feature score is based on a distance within a medical ontology between the feature and a medical condition;
       expand the feature sets with at least one feature similar to a corresponding feature of the feature sets, wherein the corresponding feature includes one from a group of hobby related activities and occupational related activities, and wherein the similarity of the at least one feature is based on a distance within a first ontology from the corresponding feature;
       map the identified risk factors of the activities to one or more medical tests for the associated medical conditions by training a machine learning model with the feature sets of the identified risk factors;
       analyze at least one data source about a patient to determine patient activities and generate a feature set for the patient based on the determined activities, wherein the at least one data source includes a social media network indicating the patient activities including one or more selected from a group of hobby related activities and occupational related activities; and determine the one or more medical tests to conduct from the mapping based on the risk factors associated with the determined activities of the patient by:
  determining a confidence score for the risk factors associated with the determined activities of the patient;
  applying the feature set for the patient based on the determined patient activities and the confidence score for the risk factors associated with the determined activities of the patient to the machine learning model to provide the one or more medical tests to conduct;
  validating the one or more medical tests provided by the machine learning model against prior performance for the patient, prior recommendation to the patient, and prior feedback received from a medical service provider for the patient; and
  removing at least one medical test that failed the validation from the one or more medical tests provided by the machine learning model.

14. The computer program product of claim 13, wherein the identified risk factors are concepts within a second ontology, and mapping the identified risk factors comprises:
  mapping concepts of the second ontology corresponding to the concepts of the identified risk factors to the one or more medical tests for the associated medical conditions.

15. The computer program product of claim 13, wherein the confidence score is based on one or more from a group of: concepts of an ontology present in a medical record and social media communications, a quantity of references to the concepts in the medical record and social media communications, and a distance within the ontology between the concepts and medical concepts identifying the medical tests.

16. The computer program product of claim 13, wherein the program instructions are further configured to cause the at least one processor to:
  provide evidence to support a determination of the one or more medical tests to conduct.

17. The computer program product of claim 16, wherein the evidence includes one or more from a group of: the risk factors associated with the determined activities of the patient, and the confidence score for the risk factors associated with the determined activities of the patient.

* * * * *